United States Patent
Van Eijkelenborg et al.

(10) Patent No.: US 8,926,556 B2
(45) Date of Patent: Jan. 6, 2015

(54) PRESSURE CONTROL ARRANGEMENT FOR A BREAST PUMP SYSTEM

(75) Inventors: Vivienne Veronique Van Eijkelenborg, Bilthoven (NL); Gert Bleijenburg, Bilthoven (NL); Jonathan Martinus Van Veelen, Bilthoven (NL)

(73) Assignee: Difrax Beheer B.V., BK Bilthoven (NL)

( * ) Notice: Subject to any disclaimer, the term of this patent is extended or adjusted under 35 U.S.C. 154(b) by 79 days.

(21) Appl. No.: 13/580,938

(22) PCT Filed: Feb. 24, 2011

(86) PCT No.: PCT/NL2011/050133
§ 371 (c)(1),
(2), (4) Date: Sep. 19, 2012

(87) PCT Pub. No.: WO2011/105903
PCT Pub. Date: Sep. 1, 2011

(65) Prior Publication Data
US 2013/0046234 A1    Feb. 21, 2013

(30) Foreign Application Priority Data
Feb. 25, 2010 (NL) .................................... 2004301

(51) Int. Cl.
*A61M 1/06* (2006.01)
*A61M 1/00* (2006.01)

(52) U.S. Cl.
CPC ............... *A61M 1/06* (2013.01); *A61M 1/0031* (2013.01)
USPC .......................................................... 604/74

(58) Field of Classification Search
CPC ........................................................ A61M 1/06
USPC ............................................ 604/74; 417/415
See application file for complete search history.

(56) References Cited

U.S. PATENT DOCUMENTS

| | | |
|---|---|---|
| 4,857,051 A | 8/1989 | Larsson |
| 4,929,229 A | 5/1990 | Larsson |

(Continued)

FOREIGN PATENT DOCUMENTS

CH          692323         5/2002

OTHER PUBLICATIONS

International Search Report and Written Opinion for PCT/NL2011/050133 mailed Jun. 28, 2011 in 12 pages.

(Continued)

*Primary Examiner* — Nicholas Lucchesi
*Assistant Examiner* — Melissa A Snyder
(74) *Attorney, Agent, or Firm* — Knobbe, Martens, Olson & Bear, LLP

(57) ABSTRACT

The invention relates to a pressure control arrangement for a breast pump system comprising a first pressure chamber; a first opening for receiving milk, the first opening being in connection with the pressure chamber and the first opening being arranged to have a first tube connected to the first opening; a second opening in connection with the pressure chamber, the second opening being arranged to have a second tube connected to the second opening for connecting the pressure chamber to an under pressure source; and a third opening for delivering milk to a container, the third opening comprising a first valve for closing the pressure chamber if the pressure in the pressure chamber is substantially lower than on the other side of the third opening. By providing the first pressure chamber in combination with the first valve, a space with substantially constant size is provided at each pumping cycle.

14 Claims, 2 Drawing Sheets

(56) References Cited

U.S. PATENT DOCUMENTS

| | | |
|---|---|---|
| 6,257,847 B1 * | 7/2001 | Silver et al. ............. 417/415 |
| 6,379,327 B2 | 4/2002 | Lundy |
| 6,440,100 B1 | 8/2002 | Prentiss |
| 6,673,036 B1 | 1/2004 | Britto |
| 2004/0199107 A1 | 10/2004 | Nuesch |
| 2005/0043677 A1 | 2/2005 | Kelly et al. |
| 2008/0208116 A1 | 8/2008 | Dao et al. |

OTHER PUBLICATIONS

Search Report and Written Opinion for NL 2004301 mailed Oct. 5, 2010 in 10 pages.
Office Action dated Jul. 16, 2013 for European Patent Application No. 11707714.9 in 5 pages.

* cited by examiner

PRESSURE CONTROL ARRANGEMENT FOR A BREAST PUMP SYSTEM

CROSS-REFERENCE TO RELATED APPLICATIONS

This application is the U.S. National Phase application under 35 U.S.C. §371 of International Application PCT/NL2011/050133, filed Feb. 24, 2011, which claims priority to Netherlands Application 2004301, filed Feb. 25, 2010.

FIELD OF THE INVENTION

The invention relates to the field of breast pumps.

BACKGROUND OF THE INVENTION

U.S. Pat. No. 6,379,327 discloses portable breast pump systems. A portable breast pump system disclosed comprises two breast receptors that are connected to a container by means of a collection tube. A breast pump is connected to the container by means of a vacuum tube. The collection container has a lid through which the collection tube and the vacuum tube are inserted. By operating the breast pump, a vacuum is created in an area of the collection container, causing suction to be developed through the collection tubes, resulting in the breast receptors to extract milk from a mother's breast.

A disadvantage of this portable breast pump system is that the area where vacuum is to be created is relatively large, as it is also intended for receiving milk from the mother's breast. This means that the size of the container should be at least 200 milliliters. Creating a vacuum level low enough to extract milk from the mother's breast requires either strong pumping for a small amount of time or normal pumping during a longer period in time. Pumping a long period in time is not feasible, as a mother's breast is activated best for giving milk by simulating a baby sucking on the breast. Strong pumping requires a powerful motor, requiring a significant amount of energy. This conflicts with the portable character of the portable breast pump system.

Another disadvantage is that the area in which the vacuum is to be created varies in size while more milk is collected in the collection container. This means that either the suction force applied to the mother's breast varies over time or that the suction force created by the breast pump should be varied over time. The first option is disadvantageous because this affects effective milk extraction and the second option is disadvantageous as this requires additional suction control means.

OBJECT AND SUMMARY OF THE INVENTION

It is preferred to provide a breast pump system and/or a pressure control arrangement for such system that enables more effective milk extraction compared to prior art.

In a first aspect, the invention provides a pressure control arrangement for a breast pump system comprising a first pressure chamber; a first opening for receiving milk, the first opening being in connection with the pressure chamber and the first opening being arranged to have a first tube connected to the first opening; a second opening in connection with the pressure chamber, the second opening being arranged to have a second tube connected to the second opening for connecting the pressure chamber to an underpressure source; and a third opening for delivering milk to a container, the third opening comprising a first valve for closing the pressure chamber if the pressure in the pressure chamber is substantially lower than on the other side of the third opening.

By providing the first pressure chamber in combination with the first valve, a space where lower pressure, vacuum or underpressure is to be created with substantially constant size is provided at each pumping cycle, the pumping cycle comprising a suction phase and a pause phase in which pause phase no substantial suction force is applied the pressure control arrangement via the second opening or a suction force that is at least lower than during the suction phase. This is because milk can be released from the first pressure chamber via the first valve to the container in the pause phase of each pumping cycle.

In addition, as the first pressure chamber only has to contain an amount of milk that is extracted during one pumping cycle, the pressure chamber can be kept relatively small. This in turn reduced the requirements for the pumping capacity of the underpressure source—like a pump and a suction pump in particular.

In an embodiment of the pressure control arrangement according to the invention, the second opening comprises a flow control element for impeding or preventing milk flowing from the pressure chamber through the second opening.

With the first pressure chamber comprising milk and the second opening being connected to the first pressure chamber and with an underpressure source like a suction pump being connected to the second opening, the risk occurs that milk is sucked through the second opening towards the suction pump. This may result in significant damage to the internals of the suction pump. By providing the flow control element, this risk is mitigated or at least reduced.

A further embodiment of the invention comprises a second pressure chamber between the flow control element and the second opening.

The second pressure chamber provides additional protection for milk accidentally flowing through the second opening to the underpressure source. Furthermore, it allows efficient building up and preservation of pressure in the system.

In another embodiment of the pressure control arrangement according to the invention, the flow control element comprises a fabric comprising a microporous membrane.

Microporous membranes enable a free flow of air and/or other gases through the membrane, but obstruct liquids from flowing through the membrane. This because the micropores are large enough to have gas molecules flowing through, but too small to have droplets of liquids flowing through. In this way, airflows and therefore suction action can freely move through the second opening, but liquids and in particular milk are well kept in the first pressure chamber and prevented from inflicting any damage on the suction pump or other underpressure source.

In yet another embodiment of the pressure control arrangement according to the invention, the pressure control arrangement is connected to a cap for closing a container and wherein the first opening, the second opening and the third opening are located such on the pressure control arrangement that when the cap is placed on the container, the first opening and the second opening are located outside the container and the third opening is located inside the container.

This embodiment enables easy collection of milk extracted by means of the pressure control arrangement, while the first opening and the second opening are available for connecting to an underpressure source connectable to the second opening and a milk extraction unit like a breast shell connectable to the first opening.

The invention provides in a second aspect a breast pumping system comprising: the pressure control arrangement for a breast pump system according to claim 1; a first tube connected to the first opening of the pressure chamber at a first end of the first tube; a second tube connected to the second opening of the pressure chamber at a first end of the second tube; a container for receiving milk, an opening of the container being in connection with the third opening; a first shell for accommodating the front end of a first breast connected to a second end of the first tube; and an underpressure generator connected to a second end of the second tube.

BRIEF DESCRIPTION OF THE DRAWINGS

The invention will now be discussed in further details by means of Figures. In the Figures.

DESCRIPTION OF PREFERRED EMBODIMENTS

Figure 1:
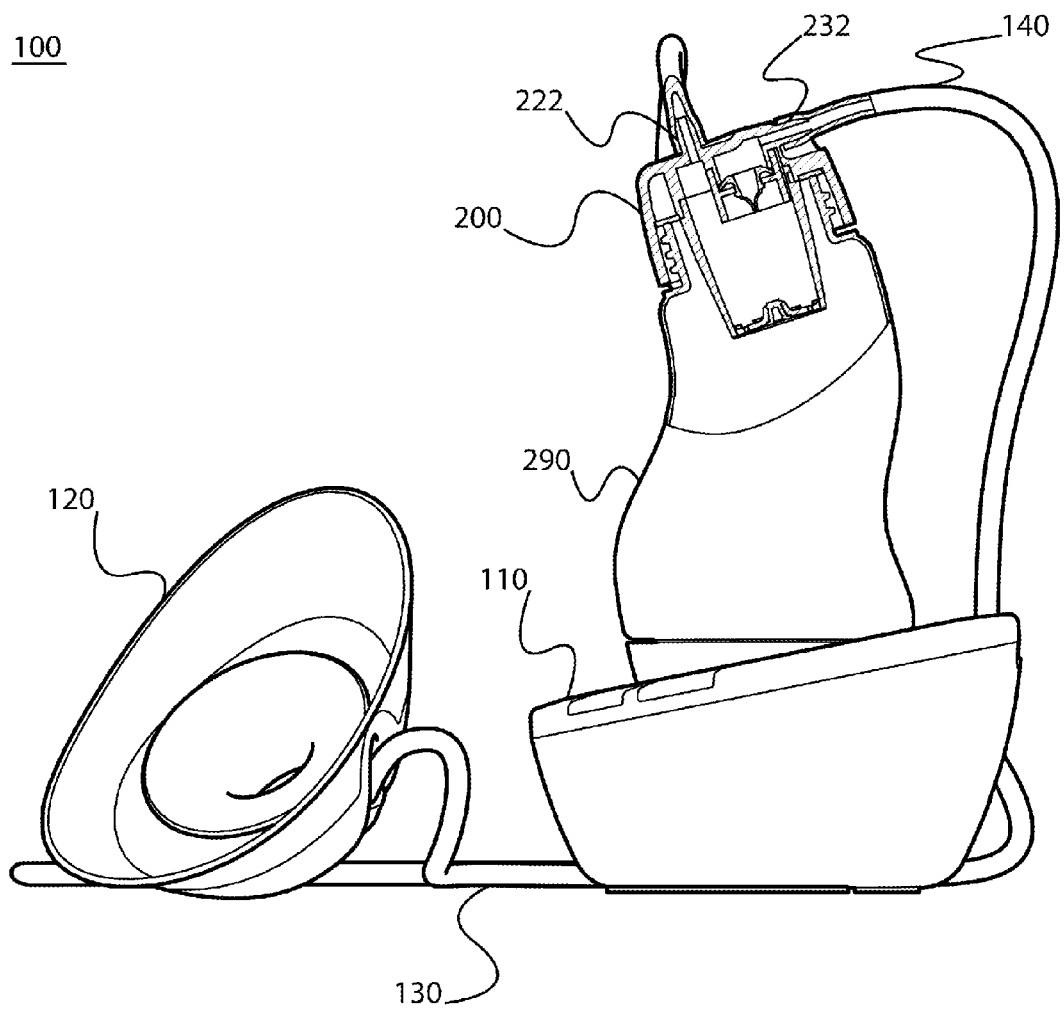
FIG. 1: shows an embodiment of the breast pump system according to the invention.

FIG. 1 shows a breast pump system 100 comprising a pump unit 110, a breast shell 120 and a bottle cap 200 fitted on a bottle 290.

The bottle cap 200 is connected to the breast shell 120 via a first tube 130 that is at one end of the first tube 130 connected to a first nozzle 222 and at a second end of the first tube 130 connected to the breast shell 120. Preferably, the second end of the first tube 130 is connected to the side of the breast shell 120 to facilitate wearing the breast shell 120, in particular underneath clothing like a bra.

The bottle cap 200 is connected to the pump unit 110 via a second tube 140. The second tube 140 is at a first end of the second tube 140 connected to the bottle cap 200 via the second nozzle 232. At a second end of the second tube 140, the second tube 140 is connected to the pump unit 110 via a pump nozzle.

Alternatively, the first tube 130 and the second tube 140 have first connectors attached to the tubes and the first nozzle 222 and the second nozzle 232 are replaced by further connectors to which the first connectors can be coupled. The second connectors can be embodied as holes for receiving the first connectors by means of a snap-on way. In that case, the first connectors are at least partially made from a resilient material like a plastic or a metal.

The pump unit 110 is arranged to provide an underpressure. In practice, this means that the pump unit 110 is arranged to provide a suction function. Preferably, this suction function is provided in a pulsed way to provide a pulsed suction airflow to a pressure control arrangement in the bottle cap 200.

Via the pressure control arrangement in the bottle cap 200 and the first tube 130, the pulsed suction airflow is transferred to the breast shell 120. With the pulsed suction airflow applied to the breast shell 120 and the breast shell 120 applied to a woman's breast, milk can be drawn from the woman's breast. That is, as a person skilled in the art will readily appreciate, only the case if the breast is able to deliver the milk. This is usually the case after a woman has given birth and the milk producing glands are regularly activated by withdrawing milk.

Figure 2:
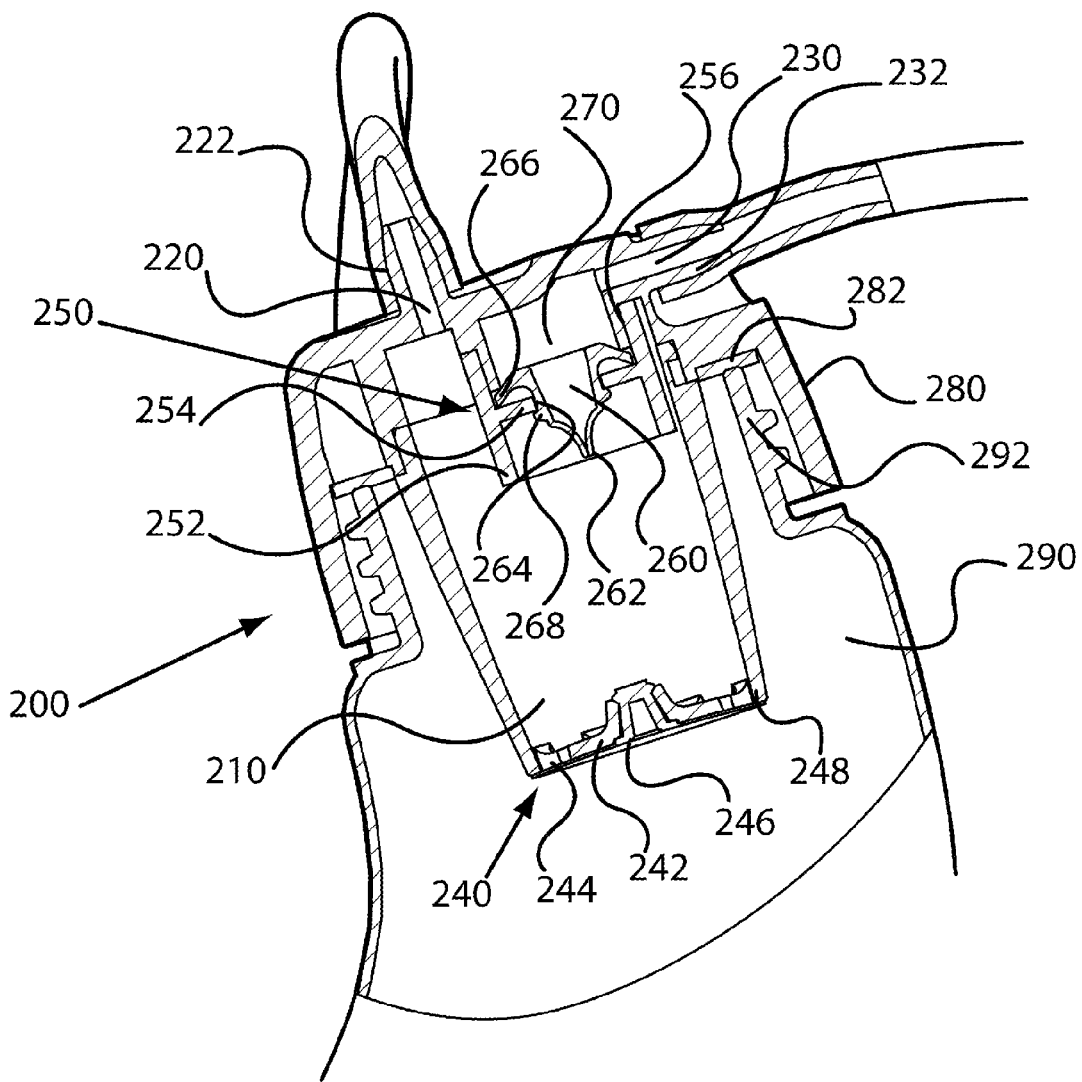
FIG. 2: shows a bottle cap comprising an embodiment of the pressure control arrangement according to the invention

FIG. 2 discloses the bottle cap 200 comprising the arrangement for controlling milk- and airflows for a breast pump in further detail. The bottle cap 200 is to be placed on the bottle 290. The bottle cap 200 comprises a first pressure chamber 210, a first opening 220 in the first nozzle 222, a second opening 230 in the second nozzle 232 and a third opening 240. The first nozzle 222 and the second nozzle 232 are arranged to have tubes fitted around them. The three openings are in connection with the first pressure chamber 210. In this embodiment, the first opening 220 is in direct contact with the first pressure chamber 210.

The third opening 240 is in connection with the first pressure chamber 210 via a first valve arrangement comprising a first valve frame 242, a membrane 244 covering the third opening 240, which membrane 244 is connected to the first valve frame 242 via a plug 246 that is connected to the membrane. Preferably, the membrane 244 and the plug 246 are provided in one piece, having the membrane 244 and the plug 246 well attached. Preferably, the membrane 244 is provided in a flexible material like silicon rubber or a thermoplastic elastomer, yielding a flexible and reliable valve functionality.

In the embodiment shown by FIG. 2, the first opening 220 and the second opening 230 are located in or adjacent to the top side of the bottle cap 200 and the third opening 240 is located at the bottom side of the bottle cap 200, opposite to the top side.

In this embodiment, the first valve arrangement is open when the pressures on both sides of the first valve arrangement are substantially the same. If the pressure in the first pressure chamber 210 is reduced, the membrane 244 moves toward a lower rim 248 of the first pressure chamber 210, thus closing the pressure chamber 210.

The second opening 230 is connected to the first pressure chamber 210 via a second valve arrangement 250. The second valve arrangement 250 comprises a second valve frame 252, the second valve frame 252 comprising a diaphragm 254. The second valve frame 252 is fit over a projection 256 which projection protrudes from the bottle cap 200. Together with the top of the bottle cap 200 and the projection 256, the second valve arrangement 250 forms a second pressure chamber 270.

The second valve arrangement 250 comprises a second valve 260 that is fit in the diaphragm 254. The valve 260 comprises a valve nozzle 262, a valve cylinder portion 264, a valve flange 266 and a valve rim 268. The valve 260 is kept in place in the diaphragm 254 by means of the valve flange 266 and the valve rim 268. Preferably, the second valve 260 is provided in a flexible material like silicon rubber or a thermoplastic elastomer, yielding a flexible and reliable valve functionality.

The bottle cap 200 further comprises a cap rim 280 that fits over a bottle rim 292 at the top of the bottle 290. Optionally, the cap rim 280 and/or the bottle rim 292 are provided with a screwing thread for securely mounting the bottle cap 200 to the bottle 290. Within the cap rim 280, an O-ring 282 is provided. Preferably, the O-ring 282 is provided in a flexible material like silicon rubber or a thermoplastic elastomer for sealing off the bottle 290 with the bottle cap 200 placed on the bottle 290.

The first pressure chamber 210, the openings connected thereto and the valves discussed above are envisaged to act as a pressure control arrangement for the breast pump system 100.

The transfer of the pulsed suction airflow by the pressure control arrangement in the bottle cap 200 will now be discussed in further detail by means of FIG. 1 and FIG. 2.

In this particular embodiment, the pulsed suction airflow comprises a suction phase and a pause phase. In the suction phase, the pump unit provides pumping action by applying an air suction force, thus creating an underpressure and in the pause phase, there is no pumping action. While there is no pumping action, the underpressure is realeased by providing a connection with ambient pressure. Alternatively, underpressure may either be maintained by the pump unit 110 in the breast pump system 100 and in particular in the tubes and pressure chambers thereof. In yet another alternative, during the pause phase a positive air flow is applied, i.e. an airflow is provided from the pumping unit 110 towards the bottle cap 200. In again another alternative, the pump unit 110 continues to work, though no underpressure is applied by means of the second tube 140.

Via the second tube 140, the suction force provided in the suction phase is transferred from the pump unit 110 to the second opening 230. The suction force creates an underpressure in the second pressure chamber 270, i.e. a lower pressure than in the environment directly outside the bottle cap 200—and the bottle 290. Via the second valve arrangement 250, the suction force is transferred to the first pressure chamber 210, creating an underpressure in the first pressure chamber 210.

As already discussed, underpressure in the first pressure chamber 210 with respect to pressure in the bottle 290 results in the first valve arrangement closing the third opening 240 by means of the membrane 244. To facilitate an airflow from the first pressure chamber 210 to the second pressure chamber 270 by means of the suction force, grooves or other passages may be provided in the diaphragm 254, the valve flange 266 and/or the valve rim 268. The grooves or other passages facilitate the airflow from the first pressure chamber 210 to the second pressure chamber 270 along the surface of the flange 266 in case the surface of the flange 266 is pressed tightly against the rim of the projection 256 or the diaphragm 254 and in case the valve rim 268 is pressed tightly against the diaphragm 254.

The underpressure in the first pressure chamber 210 results in a suction force applied to the first opening 220. This suction force is transferred to the breast shell 120 via the first tube 130. The suction force applied to the breast shell 120 results in expressing milk from a breast of a user of the breast pump system 100. By means of the suction forces in the breast pump system 100, the milk is transferred to the first pressure chamber 210.

As long as the pump unit 110 provides a suction force, milk accumulates in the first pressure chamber 210. If the suction force falls away in a pause phase of the pump unit 110, the pump unit 110 enables in this embodiment the pressure in the tubes and pressure chambers of the breast pump system 100 to return to ambient (i.e. the pressure of the environment directly outside the breast pump system 100) by providing an open connection between the outside environment and the second tube 140.

At the end of the suction phase, at the start of the pause phase, the pressure in the second tube is higher than in the second pressure chamber 270. This results in an air flow from the pump unit 110 via the second tube 140 towards the second pressure chamber 270. In turn, as this results in the second pressure chamber 270 having a higher pressure than the first pressure chamber 210, in an airflow from the second pressure chamber 270 to the first pressure chamber 210 via the valve nozzle 262.

As the pressure in the first pressure chamber 210 returns to ambient pressure, the first valve arrangement opens as the force pulling the membrane 244 towards the lower rim 248 of the first pressure chamber 210 is removed.

Additionally or advantageously, the membrane 244 moves away from the lower rim 248 by virtue of the force of gravity acting on the milk accumulated on top of the membrane 244. Hence, it is possible to have the first valve arrangement to be closed if the pressures on both sides of the membrane are the same. It is stipulated, however, that with a relatively sticky substance like human milk, this configuration creates the risk of the membrane 244 being stuck against the lower rim 248 in a stationary situation.

In this way, milk accumulated in the first pressure chamber flows in the bottle 290—or another container in connection with the first the third opening 240 of the pressure chamber 210.

It is important that the first pressure chamber 210 is large enough to accommodate an amount of milk that is drawn from the user's breast in one suction phase. On the other hand, the first pressure chamber 210 should be small enough to enable the pump unit 110 to create an underpressure that is large enough—or actually low enough—to draw milk from the user's breast. For building up the underpressure in the first pressure chamber 210 and spaces in connection with the first pressure chamber 210 like the first tube 130, the second pressure chamber 270 and the second tube 140, either the suction power of the pump unit 110 should be high enough and the various spaces mentioned above should in total be small enough. This provides a person skilled in the art with a certain amount of parameters to properly dimension the length of the tubes, the sizes of the pressure chambers and/or the strength of the pump unit 110.

Additionally or alternatively, also the length of the suction phase can be changed as the length of the suction phase also determines how much air is sucked out of the total of spaces into the pump unit 110. However, it is stipulated that this degree of freedom does not leave a lot of space for engineering as the pulsed suction process of the pump unit 110 should simulate the sucking of a baby to a woman's breast as much as possible for optimal application of the breast pump system 100.

Additionally, the airflow flows further through the first tube 130, thus resulting in an increased pressure in the first tube 130 and the breast shell 120, preferably rising to ambient level in order to relieve the woman's breast to which the breast shell 120 is connected. Alternatively, the pressure in the breast shell 120 returns to a level just below ambient, to ensure the breast shell 120 to remain fixed to the woman's breast.

The second valve arrangement 250 prevents milk accumulated in the first pressure chamber 210 from flowing to the pump unit 110, as milk may damage the internal mechanisms of the pump unit 110. The valve nozzle 262 is normally closed and only opened to enable an airflow from the second pressure chamber 270 to the first pressure chamber. Furthermore, the valve flange 266 and the valve rim 268 close the diaphragm 254 such that air can flow from the first pressure chamber 210 to the second pressure chamber 270 without obstruction or at least without significant obstruction, but also in such a way that liquids like milk cannot pass from the first pressure chamber 210 to the second pressure chamber 270 or at least not in quantities large enough to damage the internal mechanisms of the pump unit 110.

As an alternative to the second valve arrangement 250, the boundary between the first pressure chamber 210 and the second pressure chamber 270 is in another embodiment provided with a microporous membrane. Such a microporous membrane is preferably, though not necessarily, provided with a fabric liner. Such fabric with a microporous membrane is commercially available under the name Gore-Tex® and other trademarks. Microporous membranes have typically about a billion pores per square centimeter, with each pore having a size that is significantly smaller than a water droplet. Typical ratios are pores that are between 1/10.000 and 1/30.000 the size of a water droplet. In this way, the fabric allows air to flow freely from the first pressure chamber 210 to the second pressure chamber 270 and vice-versa. On the other hand, milk and other liquids are kept well away from the internal mechanisms of the pump unit 110.

The second valve arrangement 250 is primarily provided to prevent milk flowing from the first pressure chamber 210 to the pump unit 110. Working embodiments of the pressure control arrangement according to the invention can be implemented without the second pressure chamber 270 and the second valve arrangement.

The second pressure chamber 270 is primarily provided to accommodate the valve 260. If a smaller valve is used or a microporous membrane is used between the second tube 140 and the first pressure chamber 210, such smaller valve or the microporous membrane can alternatively be placed directly in or in front of the second opening 230, thus omitting the second pressure chamber 270.

In addition to the breast shell 120 being comprised by the breast pump system 100, in a further embodiment a further breast shell is provided that is also connected to the pressure control arrangement for a breast pump comprised by the bottle cap 200. This connection can be established by providing a fourth opening that is in correspondence with the first pressure chamber 210, which fourth opening is connected to a nozzle for connecting a tube that can in turn be connected to the further breast shell.

Alternatively, the first tube 130 is split in two tubes. Of those two tubes, a first is connected to the breast shell 120 and a three-way splitter and a second one is connected to the three-way splitter and the first nozzle 222. The further breast shell is connected to the three-way splitter and to the further breast shell. The three-way splitter can be embodied by providing three nozzles or cavities arranged such that openings of the nozzles or cavities meet on one side of the nozzle or cavity and other sides of the nozzle or cavity point outwardly to have a tube connected to each open end of the nozzle or cavity, for either directly connecting the tube or for connecting a connector attached to the tube, as discussed above. Alternatively, the three-way splitter is embodied as one nozzle or cavity with a further nozzle or cavity connected to that nozzle or cavity, the opening of the further nozzle or cavity being connected to the opening of the earlier nozzle or cavity.

In the embodiments disclosed, the pressure control arrangement is comprised in the bottle cap 200. It is noted that the pressure control arrangement may also be provided without the cap rim 280 for screwing the pressure control arrangement on the bottle 290. Instead, a tube could be connected to the third opening 240 and the tube is in turn connected to a container like the bottle 290 or another container suitable for receiving human milk.

Though the invention and the embodiments disclosed and discussed is particularly suitable for extracting and/or arranging the extraction of milk from a mother's breast, it may also be used for extracting and/or arranging the extraction of milk from other mammals.

A person skilled in the art will readily appreciate that various parameters disclosed in the description may be modified and that various embodiments disclosed and/or claimed may be combined without departing from the scope of the invention.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

In the description above, it will be understood that when an element such as layer, region or substrate is referred to as being on or onto another element, the element is either directly on the other element, or intervening elements may also be present. In addition, it will be understood that when a first element is in connection with or coupled to a second element, the first element may be directly connected to the second element, fixed or detachable, or connected via a third element, while the first element and the second element are still enabled to interact.

Furthermore, the invention may also be embodied with less components than provided in the embodiments described here, wherein one component carries out multiple functions. Just as well may the invention be embodied using more elements than depicted in FIG. 1 and FIG. 2, wherein functions carried out by one component in the embodiment provided are distributed over multiple components.

It is stipulated that the reference signs in the claims do not limit the scope of the claims, but are merely inserted to enhance the legibility of the claims.

This patent application claims priority of Dutch patent application N2004301, which is incorporated herein by reference.

The invention claimed is:

1. Pressure control arrangement for a breast pump system comprising:
   a) a first pressure chamber;
   b) a second pressure chamber connected to the first pressure chamber via a flow control element disposed between the first pressure chamber and the second pressure chamber, the flow control element being arranged for impeding or preventing milk flowing from the first pressure chamber to the second pressure chamber;
   c) a first opening for receiving milk, the first opening being in connection with the first pressure chamber and the first opening being arranged to have a first flexible tube connected to the first opening;
   d) a second opening in connection with the second pressure chamber, the second opening being arranged to have a second flexible tube connected to the second opening for connecting the first pressure chamber to an underpressure source; and
   e) a third opening for delivering milk to a container, the third opening being in connection with the first pressure chamber and the third opening comprising a first valve for closing the third opening if the pressure in the first pressure chamber is substantially lower than on the other side of the third opening;
   wherein the first flexible tube and the second flexible tube have a length that is significantly larger than a diameter of the respective tube.

2. Pressure control arrangement according to claim 1, wherein the flow control element comprises a further valve.

3. Pressure control arrangement according to claim 2, wherein the further valve is provided in a flexible material and comprises a further valve opening in a nozzle protruding in the first pressure chamber for enabling an air flow from the second pressure chamber to the first pressure chamber and inhibiting an air flow from the second pressure chamber to the first pressure chamber through said further valve opening.

4. Pressure control arrangement according to claim 2, wherein the further valve is arranged in an opening between the first pressure chamber and the second pressure chamber such that an air flow from the first pressure chamber to the second pressure chamber is enabled and an air flow from the second pressure chamber to the first pressure chamber is inhibited between the boundary of the opening and the further valve.

5. Pressure control arrangement according to claim 1, wherein the flow control element comprises a fabric comprising a microporous membrane.

6. Pressure control arrangement according to claim 5, wherein the membrane comprises a liner comprising polytetrafluoroethylene.

7. Pressure control arrangement according to claim 1, wherein the first opening and the second opening are located at or adjacent to a first side of the first pressure chamber and the third opening is located at or adjacent to a second side of the first pressure chamber, the second side of the first pressure chamber being opposite to the first side of the first pressure chamber.

8. Pressure control arrangement according to claim 1, wherein the pressure control arrangement is connected to a cap for closing a container and wherein the first opening, the second opening and the third opening are located such on the pressure control arrangement that when the cap is placed on the container, the first opening and the second opening are located outside the container and the third opening is located inside the container.

9. Pressure control arrangement according to claim 1, wherein the first valve is arranged to pass through milk if milk is accumulated in the first pressure chamber.

10. Pressure control arrangement according to claim 1, wherein the first valve is arranged to open or to be open if pressure in the first pressure chamber is substantially the same or higher than pressure outside first pressure chamber.

11. Breast pumping system comprising:
    a) the pressure control arrangement for a breast pump system according to any of the preceding claims;
    b) a first tube connected to the first opening of the pressure control arrangement at a first end of the first tube;
    c) a second tube connected to the second opening of the pressure control arrangement at a first end of the second tube;
    d) a container for receiving milk, an opening of the container being in connection with the third opening;
    e) a first shell for accommodating the front end of a first breast connected to a second end of the first tube; and
    f) an underpressure generator connected to a second end of the second tube to provide underpressure to the pressure control arrangement.

12. Breast pumping system according to claim 11, further comprising
    a) a third tube connected to the first opening of the pressure control arrangement at a first end of the third tube; and
    b) a second shell for accommodating the front end of a second breast connected to a second end of the third tube.

13. Breast pumping system according to claim 12, further comprising:
    a) a tube splitter having at least three splitter openings in connection to each other; and
    b) a fourth tube connected to the first opening of the pressure control arrangement at a first end of the fourth tube and connected to a first opening of the tube splitter at a second end of the fourth tube;
    wherein the first end of the first tube is connected to a second opening of the tube splitter and the first end of the third tube is connected to a third opening of the tube splitter.

14. Breast pumping system according to claim 13, wherein at least one of the first tube and second tube is a hose or flexible tube having a length that is significantly larger than a diameter of the tube.

* * * * *